United States Patent [19]

Durant et al.

[11] 3,932,427
[45] Jan. 13, 1976

[54] PYRIDYL SUBSTITUTED AMINOALKYL-THIOUREAS AND UREAS

[75] Inventors: Graham John Durant, Welwyn Garden City; John Colin Emmett, Codicote; Charon Robin Ganellin, Welwyn Garden City, all of England

[73] Assignee: Smith Kline & French Laboratories, Inc., Welwyn Garden City, England

[22] Filed: Mar. 13, 1974

[21] Appl. No.: 450,931

Related U.S. Application Data

[63] Continuation-in-part of Ser. No. 290,584, Sept. 20, 1972, abandoned, which is a continuation-in-part of Ser. No. 230,451, Feb. 29, 1972, abandoned.

[30] Foreign Application Priority Data

Mar. 9, 1971  United Kingdom............... 6352/71
July 22, 1971  United Kingdom............. 34334/71
Feb. 3, 1972  Ireland................................ 136/72

[52] U.S. Cl.... 260/294.8 H; 424/263; 260/294.8 E; 260/295 E; 260/296 R
[51] Int. Cl.$^2$..................................... C07D 213/40
[58] Field of Search ................ 260/294.8 H, 295 E

[56] References Cited
OTHER PUBLICATIONS

Durant et al., "Chem. Abstracts", Vol. 77 (1972) p. 419, No. 164704y.

Primary Examiner—Henry R. Jiles
Assistant Examiner—Robert W. Ramsuer
Attorney, Agent, or Firm—Joan S. Keps; Richard D. Foggio; William H. Edgerton

[57] ABSTRACT

The compounds are pyridyl substituted aminoalkylthioureas and ureas which are inhibitors of H-2 histamine receptors. A compound of this invention is N-methyl-N'-[2-(2-pyridylmethylamino)ethyl]thiourea.

4 Claims, No Drawings

PYRIDYL SUBSTITUTED AMINOALKYL-THIOUREAS AND UREAS

This application is a continuation-in-part of Ser. No. 290,584 filed Sept. 20, 1972 now abandoned, which is a continuation-in-part of Ser. No. 230,451 filed Feb. 29, 1972, now abandoned.

This invention relates to pharmacologically active compounds, to pharmaceutical compositions and to methods of inhibiting H-2 histamine receptors. The compounds of the invention can exist as the addition salts but, for convenience, reference will be made throughout this specification to the parent compounds.

It has for long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated by Ash and Schild (Brit. J. Pharmac. 1966, 27, 427) as H-1. The substances of the present invention are distinguished by the fact that they act at histamine H-2 receptors which, as described by Black et al. (Nature, 1972, 236, 385), are histamine receptors other than the H-1 receptor. Thus they are of utility in inhibiting certain actions of histamine which are not inhibited by the above-mentioned antihistamines. The substances of this invention may also be of utility as inhibitors of certain actions of gastrin.

The compounds with which the present invention is concerned may be represented by the following general formula; in so far as tautomerism affects the compounds mentioned in this specification, the numbering of the nucleus has been modified accordingly;

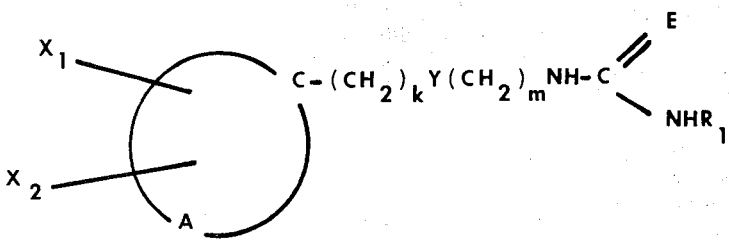

FORMULA I wherein A is such that there is formed together with the carbon atom shown a pyridine ring; $X_1$ is hydrogen, lower alkyl, hydroxyl, trifluoromethyl halogen, amino or

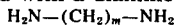

$X_2$ is hydrogen or, when $X_1$ is lower alkyl, lower alkyl or halogen; $k$ is 1 or 2 and $m$ is 2 or 3, provided that the sum of $k$ and $m$ is 3 or 4; Y is NH; E is oxygen or sulphur; and $R_1$ is hydrogen, lower alkyl, benzoyl or di-lower alkylamino-lower alkyl or a pharmaceutically acceptable addition salt thereof. Preferably A is such that the nitrogen atom is adjacent to the carbon atom shown. Preferably $X_1$ is hydrogen, methyl, bromo, amino or hydroxyl and $X_2$ is hydrogen. One group of preferred compounds within the present invention is that wherein E is sulphur; $k$ is 1, $m$ is 2 and $R_1$ is methyl.

The pharmaceutical compositions of this invention comprise a pharmaceutical carrier and, as the active ingredient, a compound of formula I, in which $k$ is 0 to 2 and the other terms are as defined therein, or a pharmaceutically acceptable acid addition salt thereof.

The methods of inhibiting H-2 histamine receptors in accordance with this invention comprise administering to an animal a compound which is an active ingredient of the pharmaceutical compositions of this invention.

A particular compound for the pharmaceutical composition and methods of inhibiting H-2 histamine receptors of this invention is N-methyl-N'-[3-(2-pyridylamino) propyl]thiourea.

The compounds with which the present invention is concerned may be produced by processes which commence with a substance of the following general formula:

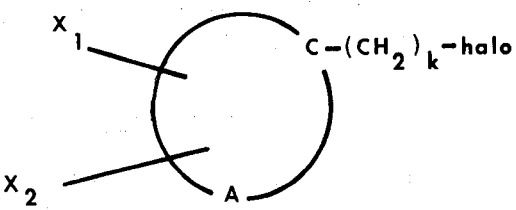

FORMULA II wherein A, $X_1$ and $X_2$ have the same significance as in formula I and $k$ is 0 to 2 except that $X_1$ may not be

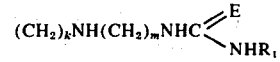

but may additionally be $(CH_2)_k$-halo. In the first stage of these processes, the compound of Formula II is reacted with a diamine of the following FORMULA III:

$$H_2N-(CH_2)_m-NH_2$$

FORMULA III wherein $m$ has the same significance as in formula I.

This reaction may be carried out under strongly basic conditions, for example in the presence of sodium ethoxide or sodium hydroxide or in an anhydrous solvent such as dimethylformamide in the presence of sodium hydride. When $k$ is 1 or 2 in formula II, one of the amino groups of the diamine of formula III may be protected by a group which will be stable under the conditions of the reaction, for example a trifluoroacetyl or a formyl protecting group may be used when the reaction is carried out under anhydrous conditions.

The amino group in the alkylene chain in the resultant intermediate is protected for the second stage of the process, which should then also be carried out under anhydrous conditions, the protecting group being finally removed, e.g., by treatment with dilute hydrochloric acid.

The intermediate product produced by these processes is of the following formula IV:

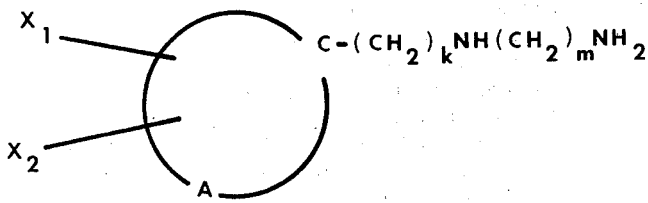

FORMULA IV wherein the amino group in the alkylene chain may be protected when $k$ is 1 to 2 and optionally the terminal amino group may also be protected and A, $X_1$, $X_2$ and $m$ have the same significance as in formula I and $k$ is 0 to 2, except that $X_1$ may not be

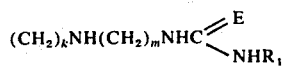

but may additionally be $(CH_2)_kNH(CH_2)_mNH_2$.

The compounds of formula I where $R_1$ is hydrogen and E is sulphur may be prepared from an amine of formula IV by reaction with an acyl isothiocyanate, e.g., benzoyl isothiocyanate, in an appropriate solvent such as chloroform. Alakline hydrolysis of these compounds, e.g., the benzoyl derivatives where $R_1$ is $C_6H_5CO$, with a reagent such as aqueous potassium hydroxide or aqueous potassium carbonate yields the compounds of formula I wherein $R_1$ is hydrogen and E is sulphur.

Compounds of formula I wherein $R_1$ is hydrogen and E is sulphur may alternatively be prepared directly from the amine of formula IV by reaction at elevated temperature with the thiocyanate of ammonium or of a metal such as sodium or potassium.

The compounds of formula I where $R_1$ is lower alkyl or dialkylaminoalkyl and E is sulphur may be prepared from the amine of formula IV by reaction with an isothiocyanic ester of formula $R_1$—N=C=S in an appropriate solvent such as chloroform, ethanol, isopropanol, acetonitrile or water.

Alternatively the amine of formula IV may be converted by reaction with carbon disulphide to the dithiocarbamic acid of the formula:

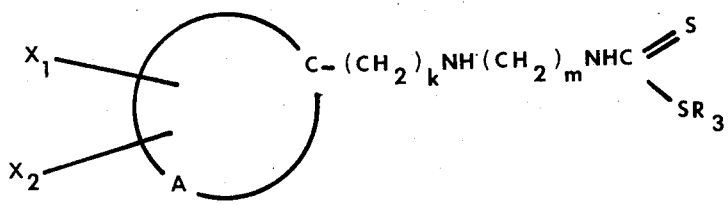

FORMULA V wherein A, $X_1$, $X_2$, $k$ and $m$ have the same significance as in formula IV and $R_3$ is hydrogen and then methylated to yield the compound of formula V wherein $R_3$ is methyl. Finally, reaction of this methyl ester with an amine of formula $R_1NH_2$, wherein $R_1$ is lower alkyl yields the required compound.

Compounds of formula I wherein E is oxygen may be formed from the amines of formula IV by treatment thereof with an isocyanate of formula $R_1NCO$ wherein $R_1$ is lower alkyl, benzoyl or dialkylaminoalkyl. The compounds of formula I wherein E is oxygen and $R_1$ is hydrogen may be obtained by reaction of the said amines with sodium or potassium cyanate.

Any N-protecting groups which may have been used can, as stated above, be removed at this stage, e.g., in the case of N-formyl or N-trifluoroacetyl groups by dilute aqueous acid treatment. If no N-protecting groups have been used, a mixture of the desired product of formula I and the corresponding bis-thiourea or bis-urea may be formed from which the former can be separated, e.g., by chromatography.

As stated above, the compounds represented by formula I have been found to have pharmacological activity in the animal body as antagonists to certain actions of histamine which are not blocked by antihistamines such as mepyramine. For example, they have been found to inhibit selectively the histamine-stimulated secretion of gastric acid from the perfused stomachs of rats anaesthetised with urethane, at doses of from about 8 and 256 micromoles per kilogram intravenously. Similarly, the action of these compounds is demonstrated by their antagonism to the effects of histamine on other tissues which, according to the above-mentioned paper of Ash & Schild, are not H-1 receptors. Examples of such tissues are perfused isolated guinea-pig heart, isolated guinea-pig right atrium and isolated rat uterus. The compounds of the invention have also been found to inhibit the secretion of gastric acid stimulated by pentagastrin or by food. In addition to the above the compounds of the invention also shpw anti-inflammatory activity in conventional tests such as the rat paw oedema test at doses of about 500 micromoles/kg. subcutaneously.

The level of activity found for the compositions comprising the compounds of the present invention is illustrated by the effective dose range in the anaesthetised rat, as mentioned above of from about 8 to 256 micromoles per kilogram, given intravenously, and also by the dose effective in the rat paw oedema test.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg. to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 mg. to about 250 mg., most preferably from about 100 mg. to about 200 mg.

The active ingredients will preferably be administered in equal doses one to three times per day. The daily dosage regimen will preferably be from about 150 mg. to about 750 mg., most preferably from about 300 mg. to about 600 mg.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric, picric and maleic acids.

Other pharmaceutically active compounds may in certain cases be included in the composition. Advantageously the composition will be made up in a dosage unit form appropriate to the desired mode of administration, for example as a tablet, capsule, injectable solution or, when used as an anti-inflammatory agent, as a cream for topical administration.

The invention is illustrated but in no way limited by the following examples.

EXAMPLE 1

N-Methyl-N'-[3-(2-pyridylamino)propyl]thiourea

A solution of 2-(3-aminopropylamino)pyridine (2.74 g.) and methyl isothiocyanate (1.46 g.) in isopropyl alcohol (50 ml.) was stirred at room temperature for 16 hours. Concentration, followed by trituration of the residue under methyl ethyl ketone gave the crude product which was recrystallised from aqueous ethanol to give N-methyl-N'-[3-(2-pyridylamino)propyl]thiourea (2,45 g.), m.p. 134°–135°. (Found: C, 53.4; H, 7.2; N, 25.0; S, 14.3. $C_{10}H_{16}N_4S$ requires: C, 53.5; H, 7.2; N, 25.0; S, 14.3).

EXAMPLE 2

N-Methyl-N'-[2-(4-pyridylmethylamino)ethyl]thiourea

Methylisothiocyanate (1.46 g.) was added slowly to a solution of N-(4-picolyl)ethylenediamine (3.3 g.) in ethanol (25 ml.) The mixture was heated under reflux for 0.5 hours concentrated and extracted with isopropyl acetate to remove N-4-picolyl-N,N'-dimethylethane-1,2-bis thiourea (m.p. 173°–174°). The mother liquors were concentrated and the residue purified by column chromatography to afford the title compound.

EXAMPLE 3

N-Methyl-N'-[2-((3-bromo-2-pyridyl)methylamino)ethyl]thiourea i. A solution of 3-bromo-2-bromomethylpyridine hydrobromide (2.53 g.) in ethanol was added slowly to excess ethylenediamine (6.0 g.) in ethanol (25 ml.) The solution was heated at 55° for 1 hour, concentrated under reduced pressure and basified with sodium hydroxide. Evaporation under high vacuo and steam distillation followed by concentration to dryness, extraction with ethanol and acidification with ethanolic hydrogen chloride affored N-3-bromo-2-picolyl ethylene diamine hydrochloride.

ii. Methyl isothiocyanate (0.73 g.) was added slowly to a solution of N-3-bromo-2-picolylethylenediamine (2.4 g.) in ethanol (30 ml.). The mixture was heated under reflux for 0.5 hours, concentrated and the crude mixture separated by column chromatography to give N-methyl-N'-[2-(3-bromo-2-pyridyl)methylamino)ethyl]thiourea.

EXAMPLE 4

N-Methyl-N'-[2-(2-pyridylmethylamino)ethyl]thiourea

Sodium hydride (54% suspension in mineral oil, 4.5 g.) is added to a solution of N-trifluoroacetylethylenediamine (15.6 g.) in dry dimethylformamide under a nitrogen atmosphere. 2-Bromomethylpyridine (17.2 g.) was added slowly and the mixture set aside overnight at room temperature. The solvent was removed under reduced pressure and the residue dissolved in a small volume of water and extracted with chloroform. The chloroform extracts were dried over anhydrous sodium sulphate, filtered and methyl isothiocyanate (7.3 g.) added and the mixture is heated at reflux for 30 minutes. Concentration under reduced pressure, treatment with aqueous hydrogen chloride and basification with potassium carbonate affords the title compound.

EXAMPLE 5

Using 3-bromomethylpyridine in the procedure of Example 4, the product is N-methyl-N'-[2-(3-pyridylmethylamino)ethyl]thiourea.

EXAMPLE 6

Using the procedure of Example 3 in place of 3-bromo-2-bromomethylpyridine the following compounds (which may be prepared from the corresponding hydroxymethylpyridines by treatment with thionyl bromide):

2-bromomethyl-3-methylpyridine
2-bromomethyl-6-methylpyridine
2-bromomethyl-3-hydroxypyridine
2-bromomethyl-3-aminopyridine
2-bromomethyl-5-hydroxypyridine 2-bromomethyl-5-trifluoromethylpyridine
2-bromomethyl-4,6-dimethylpyridine
2-bromomethyl-4-chloro-6-methylpyridine
2,6-di(bromomethyl)pyridine
the products are, respectively:
N-methyl-N'-[2-((3-methyl-2-pyridylmethyl)amino)ethyl]thiourea
N-methyl-N'-[2-((6-methyl-2-pyridylmethyl)amino)ethyl]thiourea
N-methyl-N'-[2-((3-hydroxy-2-pyridylmethyl)amino)ethyl]thiourea
N-methyl-N'-[2-((3-amino-2-pyridylmethyl)amino)ethyl]thiourea
N-methyl-N'-[2-((5-hydroxy-2-pyridylmethyl)amino)ethyl]thiourea
N-methyl-N'-[2-((5-trifluoromethyl-2-pyridylmethyl)amino)ethyl]thiourea.
N-methyl-N'-[2-((4,6-dimethyl-2-pyridylmethyl)amino)ethyl]thiourea
N-methyl-N'-[2-((4-chloro-6-methyl-2-pyridylmethyl)amino)ethyl]thiourea
2,6-bis[2-(N-methylthioureido)ethylaminomethyl]pyridine

EXAMPLE 7

N-Methyl-N'-[2-(2-(2-pyridyl)ethylamino)ethyl]thiourea

Using 2-(2-chlorethyl)pyridine in place of 3-bromo-2-bromomethylpyridine in the procedure of Example 3, the product is N-methyl-N'-[2-(2-(2-pyridyl)ethylamino)ethyl]thiourea.

EXAMPLE 8

N-methyl-N'-[2-(2-pyridylmethylamino)ethyl]urea

A mixture of N-formyl-N-(2-pyridylmethyl)ethylenediamine (prepared by adding sodium hydride to N-formylethylenediamine in dry dimethyl formamide, then reacting with 2-bromomethylpyridine at room temperature) and methyl isocyanate in dry chloroform is heated in a pressure vessel at 100° for 18 hours to give after cooling and removing the solvent N-methyl-N'-[2-((N''-formyl-N''-2-pyridylmethyl)amino)ethyl]urea. Acid hydrolysis by the procedure of Example 4 gives the title compound.

EXAMPLE 9

N-[3-(2-Pyridylamino)propyl]thiourea

A mixture of 2-(3-aminopropylamino)pyridine (6 g.) and benzoyl isothiocyanate (6.0 g.) in chloroform (150 ml.) is heated under reflux for one hour and concentrated to give N-benzoyl-N'-[3-(2-pyridylamino)propyl]thiourea. The benzoyl thiourea is added to a solution of potassium carbonate (1.4 g.) in water (80 ml.) at 60°. The solution is maintained at this temperature for 1 hour, concentrated to low bulk and acidified with hydrochloric acid. Benzoic acid is removed by filtration and the filtrate is basified with potassium carbonate and concentrated under reduced pressure. Following extraction with isopropyl alcohol and concentration, the title product is obtained.

EXAMPLE 10

N-(2-Dimethylaminoethyl)-N'-[2-(2-pyridylmethylamino)ethyl]thiourea

Treatment of N-(2-pyridylmethyl)ethylenediamine with 2-dimethylaminoethyl isothiocyanate and purifying by column chromatography by the procedure of Example 3(ii) gives N-(2-dimethylaminoethyl)-N'-[2-(2-pyridylmethylamino)ethyl]thiourea.

EXAMPLE 11

Treatment of the product of Example 1 with hydrochloric acid gives the hydrochloric acid salt of N-methyl-N'-[3-(2-pyridylamino)propyl]thiourea.

EXAMPLE 12

Treatment of the product of Example 4 with picric acid in ethanol gives N-methyl-N'-[2-(2-pyridylmethylamino)ethyl]thiourea picrate.

EXAMPLE 13

| Ingredients | Amounts |
| --- | --- |
| N-methyl-N'-[3-(2-pyridylamino)propyl]thiourea | 150 mg. |
| Sucrose | 75 mg. |
| Starch | 25 mg. |
| Talc | 25 mg. |
| Stearic acid | 2 mg. |

The ingredients are screened, mixed and filled into a hard gelatin capsule.

EXAMPLE 14

| Ingredients | Amounts |
| --- | --- |
| N-methyl-N'-[2-(2-pyridylmethylamino)ethyl]thiourea | 200 mg. |
| Lactose | 100 mg. |

The ingredients are screened, mixed and filled into a hard gelatin capsule.

The pharmaceutical compositions prepared as in Examples 13 and 14 are administered to a subject within the dose ranges given hereabove to inhibit H-2 histamine receptors.

What we claim is:
1. A compound of the formula:

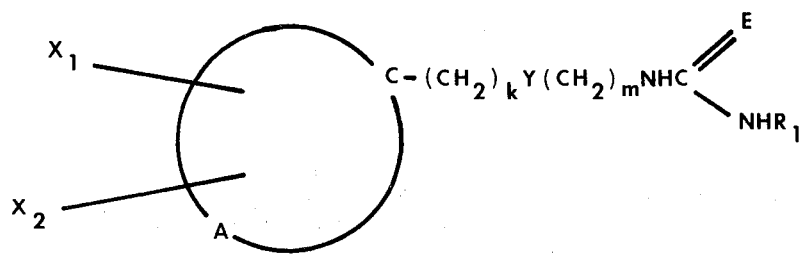

wherein A is such that there is formed together with the carbon atom shown a pyridine ring; $X_1$ is hydrogen, lower alkyl, hydroxyl, trifluoromethyl, halogen, amino or

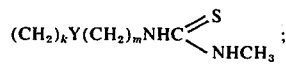

$X_2$ is hydrogen or when $X_1$ is lower alkyl, lower alkyl or halogen; $k$ is 1 or 2 and $m$ is 2 or 3, provided that the sum of $k$ and $m$ is 3 or 4; Y is NH; E is oxygen or sulphur; $R_1$ is hydrogen, lower alkyl or dimethylaminoethyl, or a pharmaceutically acceptable acid addition salt thereof.

2. A compound of claim 1 wherein $k$ is 1 and $m$ is 2.

3. A compound of claim 2 in which $X_1$ is hydrogen, methyl, bromo, hydroxyl or amino and $X_2$ is hydrogen; E is sulphur and $R_1$ is methyl.

4. A compound of claim 1, said compound being N-methyl-N'-[2-(2-pyridylmethylamino)ethyl]thiourea.

* * * * *

UNITED STATES PATENT AND TRADEMARK OFFICE
CERTIFICATE OF CORRECTION

PATENT NO. : 3,932,427

DATED : January 13, 1976

INVENTOR(S) : Graham John Durant, John Colin Emmett and Charon Robin Ganellin

It is certified that error appears in the above-identified patent and that said Letters Patent are hereby corrected as shown below:

On the first page of the patent, in the left-hand column, item [73] should read:

[73] Assignee: Smith Kline & French Laboratories Limited, Welwyn Garden City, England Column 1, line 56, after "trifluoromethyl" insert a comma.

Signed and Sealed this sixth Day of April 1976

[SEAL]

Attest:

RUTH C. MASON
Attesting Officer

C. MARSHALL DANN
Commissioner of Patents and Trademarks